United States Patent
Feltham et al.

(10) Patent No.: US 7,070,414 B1
(45) Date of Patent: Jul. 4, 2006

(54) METHOD FOR CLEANING AND STERILIZING DENTAL AND MEDICAL INSTRUMENTS

(75) Inventors: Erika B. Feltham, Fallbrook, CA (US); John W. Moers, Valley Center, CA (US)

(73) Assignee: Zila, Inc., Phoenix, AZ (US)

( * ) Notice: Subject to any disclaimer, the term of this patent is extended or adjusted under 35 U.S.C. 154(b) by 0 days.

(21) Appl. No.: 09/936,799

(22) PCT Filed: Oct. 20, 2000

(86) PCT No.: PCT/US00/29163

§ 371 (c)(1),
(2), (4) Date: Nov. 13, 2001

(87) PCT Pub. No.: WO01/56494

PCT Pub. Date: Aug. 9, 2001

Related U.S. Application Data

(63) Continuation of application No. 09/495,852, filed on Feb. 1, 2000, now abandoned.

(51) Int. Cl.
 *A61L 2/00* (2006.01)

(52) U.S. Cl. .................................... 433/229; 422/300

(58) Field of Classification Search ................. 433/163, 433/229; 24/17 B, 18, 19, 300, 301, 312, 24/16 R; 206/805; 422/26, 27, 300
See application file for complete search history.

(56) References Cited

U.S. PATENT DOCUMENTS

| | | | | |
|---|---|---|---|---|
| 2,699,585 A | * | 1/1955 | Patterson | |
| 2,969,070 A | * | 1/1961 | Todfield | |
| 5,422,067 A | * | 6/1995 | Barney | |
| 5,588,689 A | * | 12/1996 | Ochs | |
| 6,391,260 B1 | * | 5/2002 | Davis et al. | ................... 422/28 |

* cited by examiner

*Primary Examiner*—Todd E. Manahan
(74) *Attorney, Agent, or Firm*—Jeffer Mangels Butler & Marmaro, LLP

(57) ABSTRACT

An improved method for cleaning and sterilizing medical and dental instruments (16) employs the use of a banding device (10) to segregate and hold together medical or dental instruments (16) after use in a particular procedure. The banded instruments (16) are then cleaned and sterilized. This method essentially eliminates the time and effort formerly required when unsegregated instruments were mixed with other instruments for cleaning and sterilization and then stored according to the particular procedure for which they are intended and/or according to the intended particular user thereof.

4 Claims, 1 Drawing Sheet

US 7,070,414 B1

METHOD FOR CLEANING AND STERILIZING DENTAL AND MEDICAL INSTRUMENTS

This application is a continuation of Ser. No. 09/495,852 filed Feb. 1, 2000 now abandoned.

FIELD OF THE INVENTION

This invention relates generally to methods for cleaning and sterilizing medical and dental instruments.

In another respect the invention pertains to such methods employing a banding device to segregate and hold a collection of medical or dental instruments which are normally employed to effect a specific medical or dental procedure before, during and after the cleaning and sterilization thereof.

In the preferred embodiment the invention concerns methods of cleaning and sterilization of medical and dental instruments, employing an elastomeric banding device fabricated from a material that withstands the chemical and temperature conditions of cleaning and sterilization, to hold the medical or dental instruments together before, during and after the cleaning and sterilization processes.

BACKGROUND OF THE INVENTION

In the field of chair-side dentistry and in some medical procedures, each time a procedure on a patient is completed, a number of similar medical or dental instruments are left in a contaminated state. It has been the practice for many years to accumulate these instruments and periodically clean and sterilize a batch of such instruments. In dental offices in which there are several dentists, dental assistants and/or hygienists working, frequently each individual has his or her instruments which he or she prefers using. For reasons of economy, large numbers of such instruments are usually mixed together for periodic cycling through the cleaning and sterilizing processes.

After completion of such cycling, these large batches of instruments must be sorted in order to collect those instruments used in a particular procedure and in order to return them to the appropriate dentist, dental assistant or hygienist. This necessitates the expenditure of time and effort by medical or dental office personnel to perform the sorting. One procedure now used to facilitate this sorting is for each dentist or hygienist to apply a different colored band to each instrument to indicate to whom the instrument belongs. These colored bands are much easier to see than are markings made to the handles of instruments, but sorting by color is still necessary and time consuming.

The present invention provides a convenient cleaning and sterilization method that allows each group of instruments to be identified and segregated as to the particular procedure for which they are intended and even as to the person to whom they belong, so that the time and effort involved in sorting each instrument by hand is eliminated. Once collected and segregated, the method of the invention also minimizes handling of the instruments, which reduces the potential for bodily injury to the medical or dental support personnel, damage to the instruments and contamination.

SUMMARY OF THE INVENTION

Briefly, the present invention provides improvements in the prior methods for cleaning and sterilizing medical and dental instruments, which prior method includes the steps of collecting such instruments used in a plurality of medical or dental procedures after use thereof in such plurality of procedures, cleaning such collected instruments, sterilizing such cleaned instruments, segregating and sorting such sterilized instruments into groups according to the particular surgical or medical procedure for which they are intended. Our improved method comprises the steps in sequence of (a) initially banding each group of such instruments together after use thereof in a particular medical or dental procedure, such that each such banded group includes only the instruments used for that particular procedure; (b) collecting a plurality of such banded groups of instruments; (c) cleaning and sterilizing such plurality of banded groups of instruments; and (d) storing such cleaned, sterilized banded groups until the next use thereof.

In the presently preferred embodiment of the invention, our method contemplates that the bands used to hold the instruments banded in step (a) are fabricated from a material that withstands the chemical and temperature conditions of the cleaning and sterilizing steps.

In a further preferred embodiment of the invention, the bands employed are coded visually, by color or other markings, to facilitate identifying a group of instruments intended for use in a particular medical or dental procedure and/or which are intended for use by a particular clinician.

In a still further preferred embodiment, the material from which the bands are fabricated is an elastomeric material capable stretching of at least 100% and capable of withstanding temperatures in the range 212–450 degrees Fahrenheit.

In a particular preferred embodiment, the bands comprise a pair of parallel bands, a first element connecting one end of the pair of parallel bands and a second element connecting the other ends of the pair of parallel bands and each of the first and second elements have a shape and size such that one element can be inserted between the pair of bands to hold a plurality of instruments.

In the presently preferred embodiment of the invention, we use a band comprising a pair of parallel elastomeric bands having balls or enlarged elements formed at each end thereof. The device is wrapped around a group of instruments after use thereof in a particular procedure and before these instruments are to be cleaned and sterilized. One ball is inserted through the pair of bands adjacent the other ball to lock the device about the instruments. Preferably, the balls at the ends of the pair of bands are integrally molded therewith. However, separate balls or enlarge elements may be attached to the bands if desired. The material of the device is selected to provide an elongation or stretch in the range of 100% to 700%. This allows the device to be adequately stretched to surround the proper quantity of instruments. The elastomeric material selected must be capable of withstanding repeated exposure to common disinfectant compounds and the high temperatures of steam sterilization (e.g., autoclaving) or dry heat sterilization within the range of 212–450 degrees Fahrenheit. Preferably, a silicone compound material such as Dow Corning XL2488 or equivalent can be used.

The devices can be visually coded, e.g., by a plurality of colors and/or patterns, to allow easy identification of the owner of the instruments and/or the intended use of that particular group of instruments. These markings are distinctive enough to allow each clinician to quickly gather his or her instruments together, band them and send them through common office cleaning and sterilization processes while intermixed with other batches of instruments. As a result, the effort of segregating and sorting the instruments into groups intended for use in a particular medical or dental procedure and/or for use by a particular clinician is essentially eliminated. Also, handling is reduced thereby minimizing potential for bodily injury, damage to instruments and contamination. Devices can also be made with bands of different lengths and sizes to accommodate larger or smaller groups of instruments. These could be marked with letters or numbers to designate their sizes. Alternatively, the parallel bands could have interconnecting elements, similar to the rungs of a ladder, for accommodating batches of instruments of different sizes.

The balls or other enlarged elements formed at each end of the device are sized to create a proper locking by putting the ball through the opening between the two parallel bands. The bands are designed of such a shape and size to ensure adequate strength and to provide proper tension to keep the instruments contained during cleaning, sterilization and storage.

The aforementioned advantages of the present invention, as well as additional advantages thereof, will be more fully understood hereinafter as a result of a detailed description of the preferred embodiment when taken in conjunction with the following drawings.

DETAILED DESCRIPTION OF PREFERRED EMBODIMENTS

Figure 1:
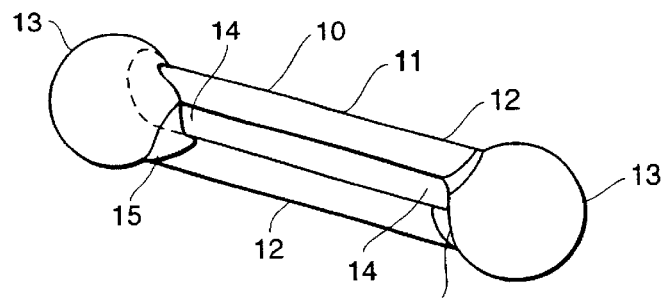
FIG. 1 is a perspective view of an elastomeric banding device which is used in accordance with the preferred embodiment of the invention.
Figure 2:
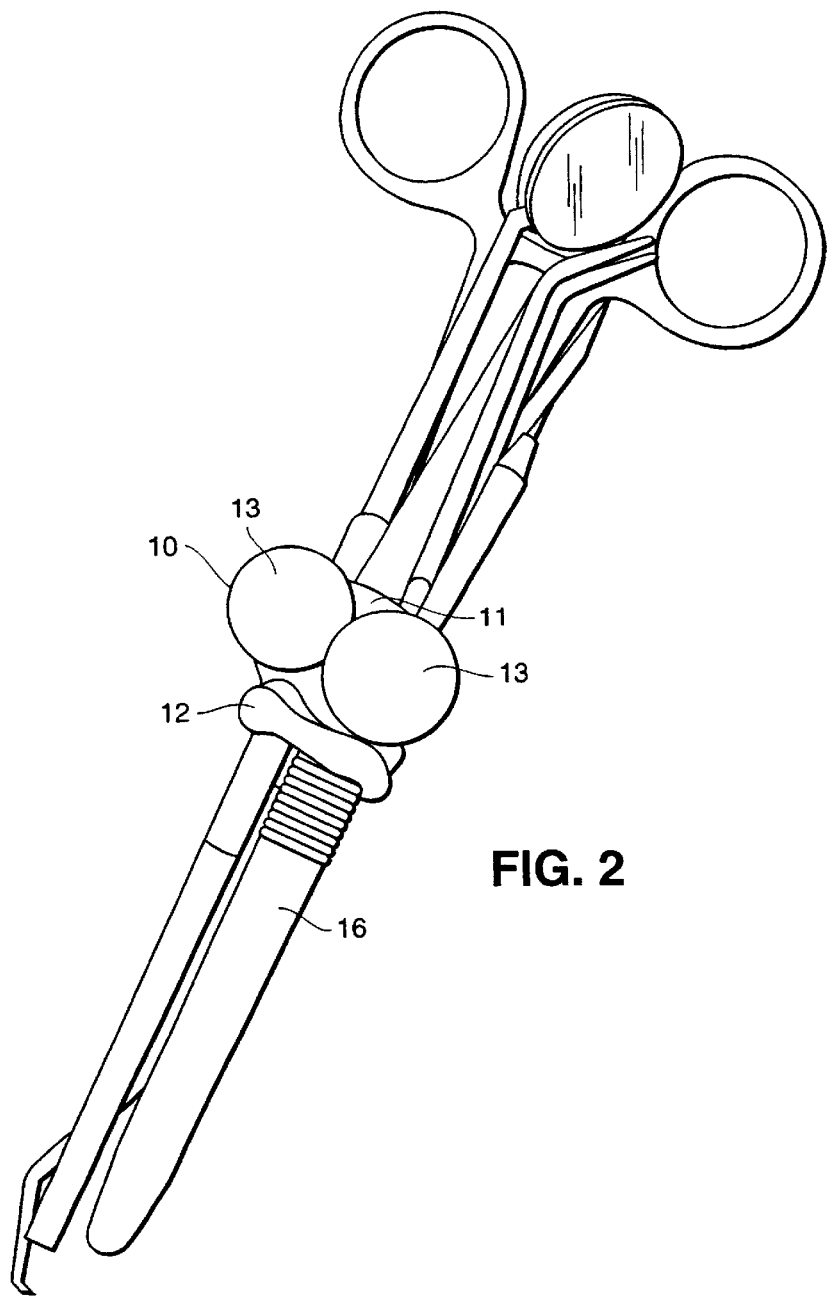
FIG. 2 is a perspective view of the elastomeric banding device of FIG. 1 wrapped around and holding a plurality of dental instruments.

FIG. 1 depicts an elastomeric banding device generally designated as 10. The device 10 has a first and second band 11 and 12. One end of each band 11 and 12 is integrally molded or otherwise connected to a ball or enlarged element 13 at each end thereof. Each ball 13 is properly sized such that it can be inserted into the opening 14 formed by the junction of the two ends of the bands 11 and 12 with one of the balls 13. The device 10 is fabricated from an elastomeric material which allows the bands 11 and 12 to adequately stretch to be able to be wrapped around a plurality of dental instruments 16 as seen in FIG. 2. The elastomeric material must be capable of withstanding steam or dry heat sterilization temperatures in the range of 212 to 450 degrees Fahrenheit. Preferably, the elastomeric material can stretch from 100% to 700%. Preferably, the elastomeric material is silicone, since silicone is not affected by the repeated processes of disinfecting and sterilization over periods of time.

The elastomeric device 10 is molded in a plurality of colors and/or patterns so that each doctor, dentist or hygienist in an office with common cleaning and sterilization equipment will have visually distinguishable banding devices. Thus, each clinician's (or clinician's assistant) of each group of instruments can wrap his or her batch of instruments together and put them through the cleaning and sterilization cycle and have them returned without any necessity for individual sorting of the instruments to segregate instruments owned or used by other clinicians and/or to segregate instruments used for other specific procedures.

While the balls or enlarged elements are shown in the Figures as being spherical, they may have other shapes, such as a rod, so long as the shape is such that it can be inserted between the bands and be captured or locked in the junction between the ends of the bands and the enlarged element to hold the batch of instruments during sterilization. Alternatively, the bands may be interconnected by rungs or cross-members not shown, which would accommodate different sized batches of instruments, and the ball would be captured or locked between the bands and the cross-member or rung.

In use, a batch of instruments to be sterilized is held in one hand. The elastomeric banding device 10 is wrapped around the instruments. One element 13 is inserted through the junction of the bands 11 and 12 and the other element 13 to hold the batch of instruments together. After sterilization, the sterilized instruments may be returned to the user thereof. Different color or patterned banding devices 10 may be used for different dentists or hygienists in one office. Alternatively, letters or numbers on the banding devices could be utilized for identification purposes.

Although the invention is described herein with reference to a specific embodiment, many modifications and variations therein will readily occur to those skilled in the art. The drawings are intended only as illustrative and are not intended as limitations on the scope of the invention, which is defined only by the following claims.

Having described our invention in such terms as to enable those skilled in the art to understand and practice it and, having identified the presently preferred embodiments thereof, we claim:

1. In a method for cleaning and sterilizing medical and dental instruments, which method includes the steps of
   collecting such instruments used in a plurality of medical or dental procedures after use thereof in such plurality of procedures,
   cleaning such collected instruments,
   sterilizing such cleaned instruments, and
   segregating and sorting such sterilized instruments into groups according to the particular surgical or medical procedure for which they are intended, and
   storing such groups of sterilized instruments until the next use thereof
the improved method comprising the steps in sequence of
   (a) initially banding each group of such instruments together after use thereof in a particular medical or dental procedure, such that each such banded group includes only the instruments used for that particular procedure;
   (b) collecting a plurality of such banded groups of instruments;
   (c) cleaning and sterilizing such plurality of banded groups of instruments; and
   (d) storing such cleaned, sterilized banded groups until the next use thereof.

2. The method of claim 1 wherein the material from which the bands fabricated is selected to withstand the chemical and temperature conditions of said cleaning and sterilizing step.

3. The method of claim 1 wherein the bands are color coded.

4. The method of claim 1 wherein the bands are fabricated from an elastomeric material capable of stretching at least 100% and capable of withstanding temperatures in the range 212–450 degrees Fahrenheit, and said bands comprise:
   a pair of parallel bands;
   a first element connected to one end of said pair of parallel bands; and a second element connected to the other ends of said pair of parallel bands;

each of said first and second elements having a shape and size such that one element can be inserted between the pair of bands to hold a plurality of instruments together during cleaning and sterilization steps.

* * * * *